United States Patent [19]

Koga

[11] Patent Number: 5,414,147
[45] Date of Patent: May 9, 1995

[54] METHOD FOR IMPROVING CONVERSION OF ISOBUTYLENE IN MTBE PROCESS

[75] Inventor: Kunio Koga, Houston, Tex.

[73] Assignee: Global Octanes Corporation, Deer Park, Tex.

[21] Appl. No.: 111,385

[22] Filed: Aug. 24, 1993

[51] Int. Cl.⁶ .............................................. C07C 41/06
[52] U.S. Cl. .................................... 568/697; 568/699
[58] Field of Search ................................ 568/697, 699

[56] References Cited

U.S. PATENT DOCUMENTS

| | | |
|---|---|---|
| 4,302,298 | 11/1981 | Mikitenko et al. . |
| 4,371,718 | 2/1983 | Hutson, Jr. . |
| 4,490,563 | 12/1984 | Van Pool et al. . |
| 4,503,265 | 3/1985 | Schleppinghoff et al. . |
| 4,665,237 | 5/1987 | Arakawa et al. . |
| 4,740,632 | 4/1988 | Anderson et al. . |
| 4,774,365 | 9/1988 | Chen et al. . |
| 4,808,270 | 2/1989 | Wernicke et al. . |
| 5,120,403 | 6/1992 | Smith, Jr. . |
| 5,160,414 | 11/1992 | Lee et al. . |

*Primary Examiner*—Howard T. Mars
*Attorney, Agent, or Firm*—Robert C. Curfiss; Butler & Binion

[57] ABSTRACT

A method for improving the conversion of isobutylene in the MTBE reaction process while simultaneously producing a substantially methanol-free MTBE utilizes an increased methanol to isobutylene molar ratio in the reaction process and methanol-free C4 hydrocarbons as reflux. The use of a methanol-free C4 hydrocarbon stream as reflux eliminates the excess methanol generated by increasing the methanol to isobutylene molar ratio without requiring a higher reflux ratio or changing operating conditions. The method permits isobutylene conversion of more than 98% while producing a purified MTBE with less than 0.5% methanol content.

13 Claims, 7 Drawing Sheets

GRAPH 1

METHOD FOR IMPROVING CONVERSION OF ISOBUTYLENE IN MTBE PROCESS

This invention is generally related to a process for the production of MTBE from isobutylene and methanol and is specifically directed to an improvement in the conversion of isobutylene in the MTBE reaction process while simultaneously producing a substantially methanol-free MTBE.

BACKGROUND OF THE INVENTION

Methyl ter-butyl ether (MTBE) is well recognized as a gasoline blending component. MTBE is desirable because it has a high octane and the oxygen in its molecule structure facilitates effective combustion of gasoline and suppresses CO formation. The use of MTBE in the production of gasoline for the protection of the environment and octane improvement has made it the fastest growing large volume chemical in the world.

MTBE is produced through the reaction of isobutylene with methanol over a catalyst. The isobutylene necessary for producing MTBE can be obtained from various sources. A common source for the isobutylene is through the dehydrogenation of isobutane. The reaction of isobutylene and methanol produces an effluent stream containing MTBE, excess methanol and miscellaneous C4 hydrocarbons. Generally, the effluent stream is fed to a debutanizer, distillation column where the MTBE product is recovered from the bottom and the remaining methanol forms an azeotrope with the C4's and is lifted overhead. Because the only method for removing methanol is by forming an azeotrope with the C4's, any excess methanol beyond that which will form an azeotrope with the C4's will be deposited in the MTBE product recovered from the bottom of the debutanizer. However, in order to meet certain purity standards, MTBE producers strive to eliminate excess methanol from the MTBE bottom product.

The technologies for producing MTBE from isobutylene are offered by several licensors. Each licensor has its own unique reaction step but utilizes a similar process for the purification of the effluent from the reactors. A conventional method for the purification of MTBE utilizes a portion of the overhead condensate as reflux to the debutanizer. U.S. Pat. No. 4,665,237 issued to Arakawa et al. on May 12, 1987, illustrates another process for producing purified MTBE through the reaction of isobutylene and methanol. In this patent, a purified MTBE is obtained by controlling the amount of methanol fed to the reaction process to an amount which will allow most of the unreacted methanol to be distilled as an azeotropic mixture with the C4 hydrocarbons.

While it is desirable to produce a substantially methanol-free MTBE, a main objective in the MTBE reaction process is to convert, as far as is possible, all isobutylene. A higher isobutylene conversion will result in the production of more MTBE. Any isobutylene which is not converted in the reaction process is typically recycled to the dehydrogenation process. The use of recycled unreacted isobutylene in the feedstock to the dehydrogenation process may cause unfavorable coke formation. Thus, in addition to producing more product, a higher isobutylene conversion would decrease the amount of unreacted isobutylene to be recycled and serve to protect the dehydrogenation process from unfavorable formations. Also, because the operating conditions of the dehydrogenation plant have been set to obtain optimum conversion while utilizing isobutane as feedstock, the introduction of recycled unreacted isobutylene into the dehydrogenation process may shift the equilibrium of the reaction and reduce the conversion rate. For these reasons, isobutylene conversion of 99% or more in the MTBE reaction process is extremely desirable.

It is well known that a large excess of methanol at the reaction stage will increase the conversion of isobutylene. With respect to the MTBE reaction process, the temperature and methanol to isobutylene molar ratio affect the conversion of isobutylene. While a lower temperature slightly favors isobutylene conversion, a high methanol to isobutylene molar ratio greatly increases the conversion of isobutylene. Therefore, increasing the methanol to isobutylene molar ratio is the most effective way to increase conversion. However, increasing the feed of methanol in the reaction process results in methanol over the amount which can form an azeotrope with the C4 hydrocarbons and the excess methanol is deposited in the MTBE product. Thus, the MTBE process cannot be operated effectively at a higher molar ratio if the increased ratio results in excess methanol content in the MTBE product.

The methanol to C4 hydrocarbon ratio at which all unreacted methanol can form an azeotrope with the C4 hydrocarbons is 0.065 at 95 psig. It has been found that utilizing a methanol to isobutylene molar ratio greater than 1.03 in the MTBE reaction will increase the unreacted methanol to C4 hydrocarbon ratio beyond the azeotropic ratio of 0.065 and will result in excess methanol in the bottom product. However, the use of a molar ratio of 1.03, even at optimized conditions, will result in an isobutylene conversion rate of less than 97%. Further, although the azeotropic concentration ratio can be increased above 0.065 by increasing the operating pressure, the increased molar ratio which can be used as a result of utilizing a higher operating pressure is not sufficient to achieve a 98% or 99% conversion of isobutylene.

An isobutylene conversion rate of more than 98% can be obtained by using a methanol to isobutylene molar ratio greater than 1.06 in the MTBE reaction process. However, increasing the methanol to isobutylene molar ratio to improve the conversion of isobutylene to more than 98% yields MTBE product with an undesirable methanol content. Conversely, utilizing a lower molar ratio, in order to maintain the methanol content at a level which can form azeotropes with the C4's, results in the decreased conversion of isobutylene.

While there are several methods for producing MTBE, the prior art MTBE production techniques do not address the problem of achieving higher conversion of isobutylene while maintaining production of MTBE with a favorable product purity. The conventional method for purifying MTBE does not effectively remove large amounts of excess methanol produced at higher isobutylene conversion rates since the overhead condensate used as reflux is already at its azeotropic concentration. Therefore, there is a need for a method which produces a substantially methanol-free MTBE while simultaneously achieving higher isobutylene conversion.

SUMMARY OF THE INVENTION

The subject invention is directed to a method for increasing the conversion rate of isobutylene in the MTBE reaction process while producing a substantially methanol-free MTBE. The subject invention utilizes an increased methanol to isobutylene molar ratio to achieve a higher conversion of isobutylene and eliminates the excess methanol generated by increasing the molar ratio by feeding a methanol-free C4 stream as reflux to the debutanizer. The use of methanol free C4's as reflux not only makes it possible to effectively operate the process and achieve more than 98% of isobutylene conversion, but also makes it possible to save energy because the reflux ratio can be reduced. The subject invention is specifically designed to produce MTBE product with a 0.5% or less methanol content while simultaneously increasing isobutylene conversion to more than 98% by raising the methanol to isobutylene molar ratio above 1.06 in the MTBE reaction process.

Isobutylene conversion can be increased from less than 97% to more than 99% by increasing the methanol to isobutylene molar ratio from 1.03 to 1.2. Although the molar ratio could be raised beyond 1.2 to more closely approach 100% of isobutylene conversion, the amount of methanol-free C4 reflux would have to be greatly increased to effectively eliminate all of the excess methanol generated by the significant increase in molar ratio required to approach a 100% conversion rate. Typically, the amount of reflux flow which can be used is limited by the capacity of the existing equipment. Thus, the upper limit of the molar ratio is defined by the capacity of the debutanizer and extractor. Theoretically, a future MTBE plant could be constructed to achieve isobutylene conversion at nearly 100% by designing a larger capacity debutanizer and extractor to accommodate the necessary reflux flow. Where a molar ratio of 1.2 or less is selected, it has been found that the use of methanol-free C4's as reflux will effectively maintain the azeotropic ratio of 0.065, without requiring the construction of a larger debutanizer and extractor, and will eliminate excess methanol to produce MTBE with a 0.5% or less methanol content.

In the preferred embodiment of the subject invention, methanol and isobutylene feedstock are fed to a MTBE reactor at a methanol to isobutylene molar ratio greater than 1.06 to achieve isobutylene conversion of more than 98%. The effluent stream from the reactor, containing MTBE, excess methanol and miscellaneous C4 hydrocarbons, is fed to a debutanizer, distillation column. In the debutanizer, an azeotropic mixture of methanol and C4 hydrocarbons is formed and lifted overhead. The overhead stream from the debutanizer is sent to a methanol extractor where the methanol is extracted with water to produce a methanol/water stream and a substantially methanol-free C4 raffinate. A portion of the raffinate is used as reflux to the debutanizer. Because methanol is removed by forming an azeotrope with the C4's, the introduction of methanol-free C4 raffinate provides the C4's necessary to remove the excess methanol generated by the increased methanol to isobutylene molar ratio in the reaction process. Thus, the use of methanol-free C4's as reflux maintains the azeotropic concentration of 0.065 necessary to produce substantially methanol-free MTBE.

While the subject invention utilizes an extractor to produce substantially methanol-free C4's, any known method which produces methanol-free C4's may be used. The crucial part of this invention is not the method for producing methanol-free C4's but the use of methanol-free C4's as reflux to the debutanizer in order to eliminate excess methanol generated by increasing the methanol to isobutylene molar ratio in the MTBE reaction process. Thus, the methanol-free C4's used as reflux can come from any known source.

In the subject invention, all or part of the raffinate from the extractor may also be fed to a dehydration tower where a small amount of oxygenates and water are removed from the raffinate. Because the raffinate from the extractor may contain a small amount of water with traces of methanol, the use of a dehydration tower removes the water thereby eliminating any traces of methanol found in the C4 raffinate. The exit liquid from the dehydration tower is then used as reflux to the debutanizer.

As is typical in the MTBE process, the subject invention may further include a method for separating the methanol from the methanol/water stream recovered from the extractor. If a methanol stripping tower is included, the methanol-free water recovered from the bottom of the tower may be recycled to the extractor to produce a methanol-free C4 stream and the methanol recovered from the top of the column may be recycled to the MTBE reaction process.

Therefore, it is an object and feature of the subject invention to provide a method for increasing the isobutylene conversion in the MTBE process while simultaneously producing a substantially methanol-free MTBE.

It is another object and feature of the subject invention to use a methanol to isobutylene molar ratio greater than 1.06 in the MTBE reaction process to achieve isobutylene conversion of more than 98%.

It is also an object and feature of the subject invention to use a methanol-free C4 stream as reflux to remove excess methanol generated by increasing the methanol to isobutylene molar ratio.

It is yet another object and feature of the subject invention to use a methanol-free C4 stream as reflux to achieve isobutylene conversion of more than 98% and produce MTBE product with a 0.5% or less methanol content.

Other objects and features will be readily apparent from the accompanying drawings and description.

DETAILED DESCRIPTION OF THE PREFERRED EMBODIMENTS

Figure 1:
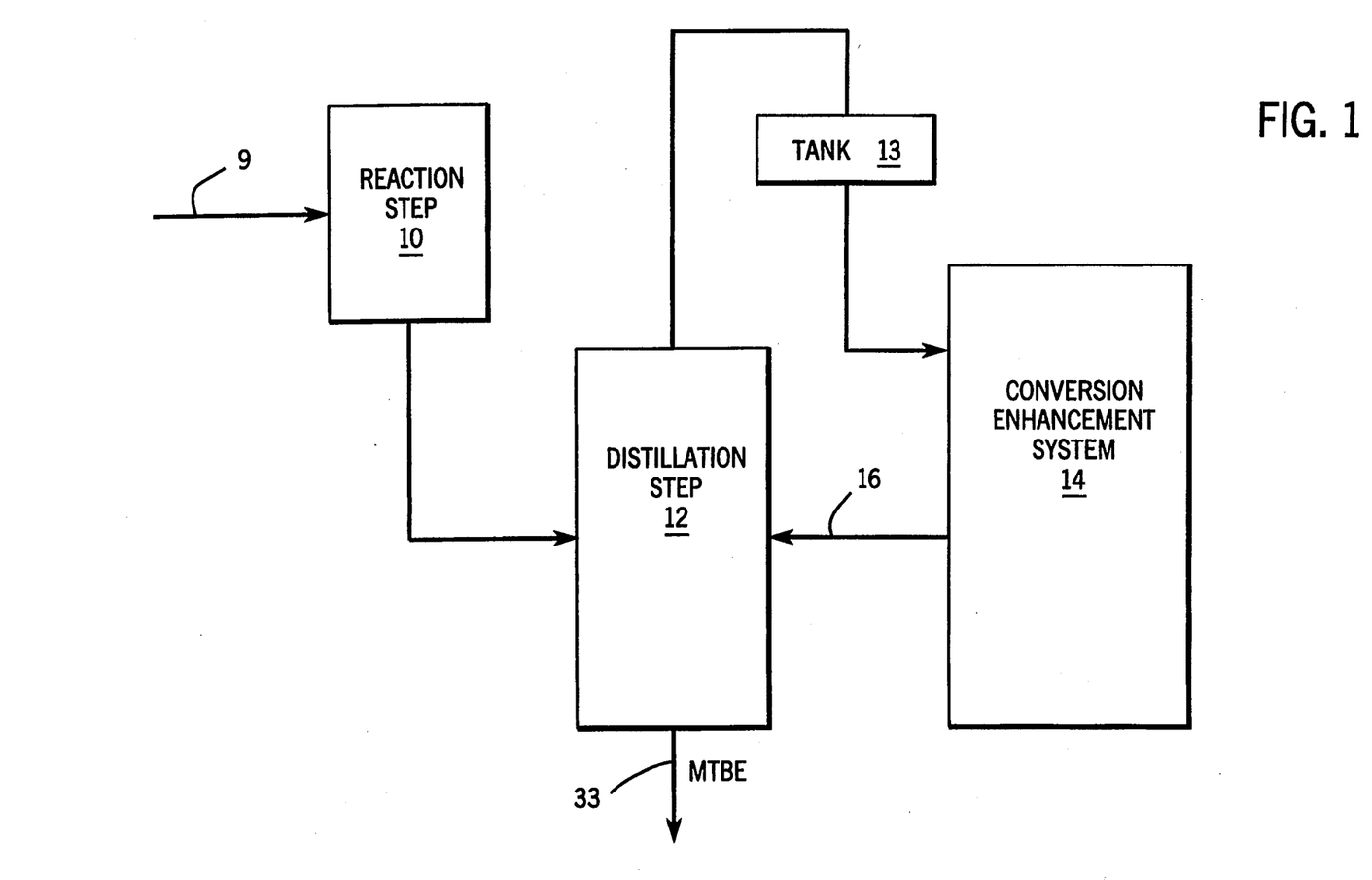
FIG. 1 is an overview of the reaction, distillation and conversion enhancement steps included in each of the three preferred embodiments of the process of the invention.

The subject invention is directed to a conversion enhancement system for removing the excess methanol generated by increasing the methanol to isobutylene molar ratio in the MTBE reaction process to produce a purified MTBE product. As shown in FIG. 1, the preferred embodiment of the subject invention includes a reaction step 10 utilizing an increased methanol to isobutylene molar ratio at 9 for improving the conversion of isobutylene, a distillation step 12, an intermediate tank 13 and the conversion enhancement system 14 The conversion enhancement system 14 consists of a methanol removal step and a dehydration step and utilizes a methanol-free C4 hydrocarbon stream obtained from either the methanol removal step or the dehydration step, or both, as reflux to the distillation step. The methanol removal step may also include a distillation process in which the methanol/water extract discarded from the methanol removal step is separated into dry methanol and methanol-free water and recycled.

As shown in FIG. 8, isobutylene conversion can be increased from less than 97% to more than 99% by increasing the methanol to isobutylene molar ratio from 1.03 to 1.2. Although the molar ratio could be raised beyond 1.2 to more closely approach 100% of isobutylene conversion, the amount of methanol-free C4 reflux would have to be greatly increased to effectively eliminate all of the excess methanol generated by the significant increase in molar ratio required to approach a 100% conversion rate. Typically, the amount of reflux flow which can be used is limited by the capacity of the existing equipment. Thus, the upper limit of the molar ratio is defined by the capacity of the debutanizer and extractor. Theoretically, a future MTBE plant could be constructed to achieve isobutylene conversion at nearly 100% by designing a larger capacity debutanizer and extractor to accommodate the necessary reflux flow. Where a molar ratio of 1.2 or less is selected, it has been found that the use of methanol-free C4's as reflux will effectively maintain the azeotropic ratio of 0.065, without requiring the construction of a larger debutanizer and extractor, and will eliminate excess methanol to produce MTBE with a 0.5% or less methanol content.

Figure 2:
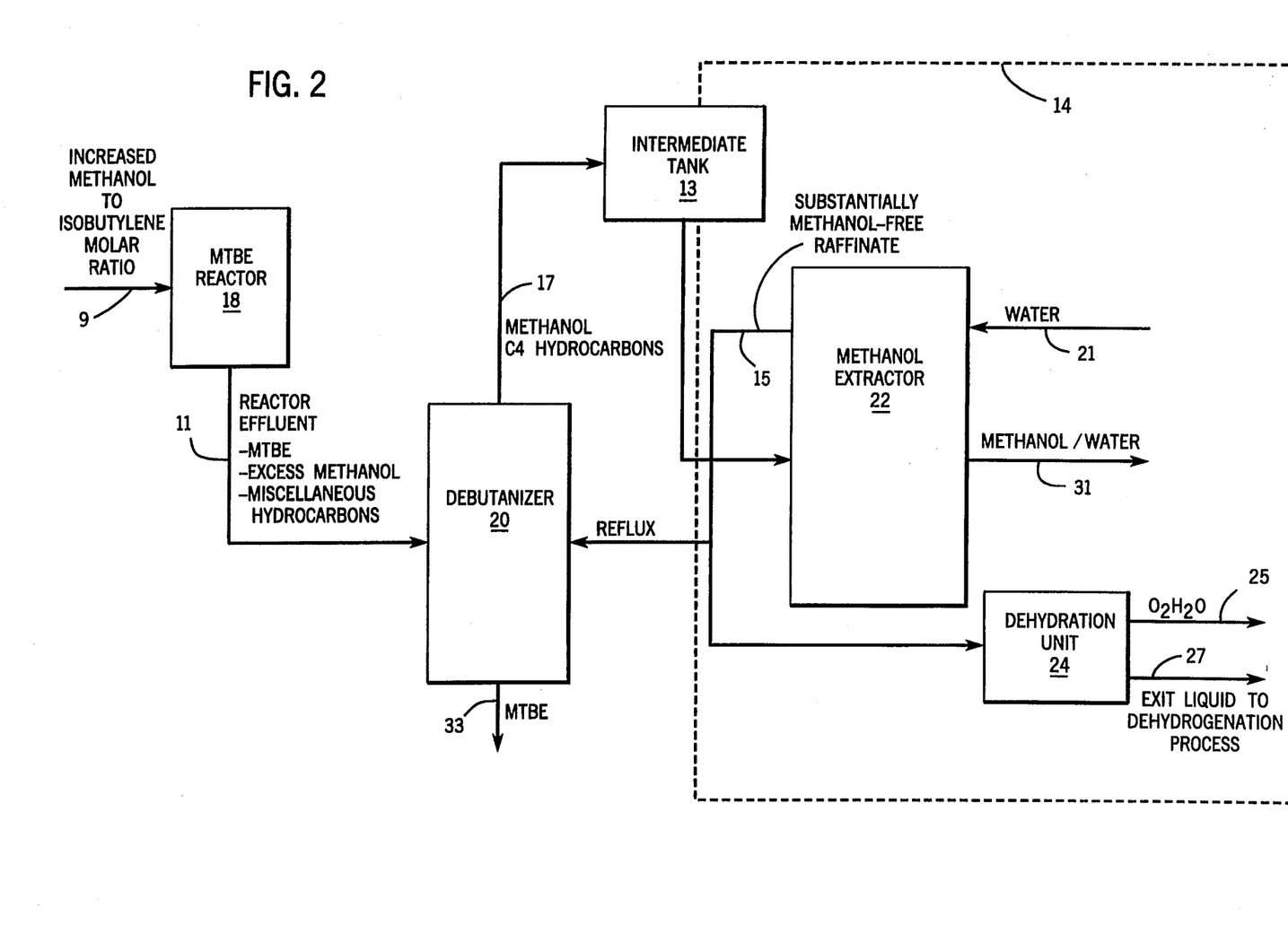
FIG. 2 is a flow chart of the process of the first preferred embodiment of the invention utilizing a substantially methanol-free raffinate from the methanol removal step as reflux to the distillation step.
Figure 3:
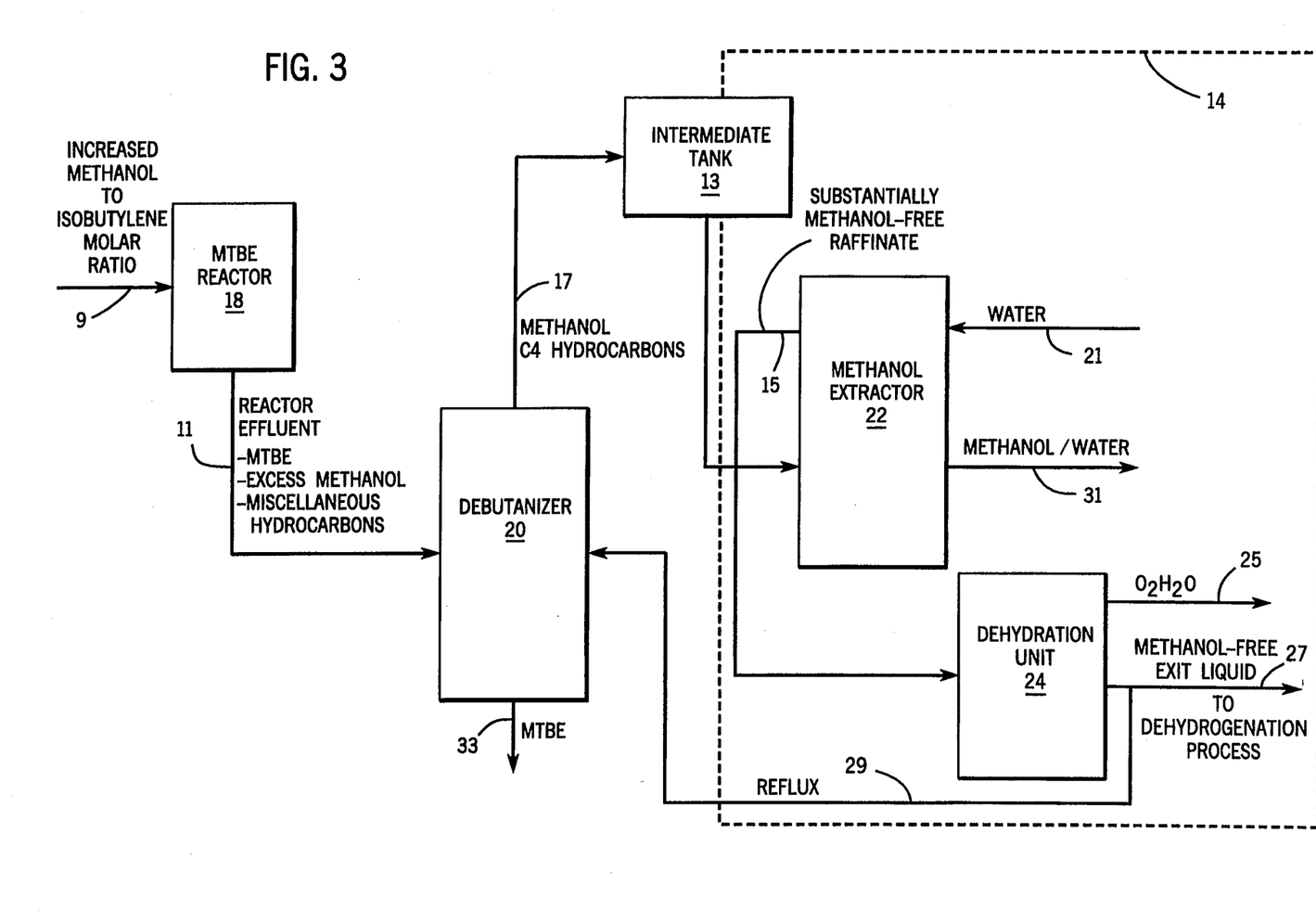
FIG. 3 is a flow chart of the process of the second preferred embodiment of the invention utilizing a methanol-free exit liquid from the dehydration step as reflux to the distillation step.
Figure 4:
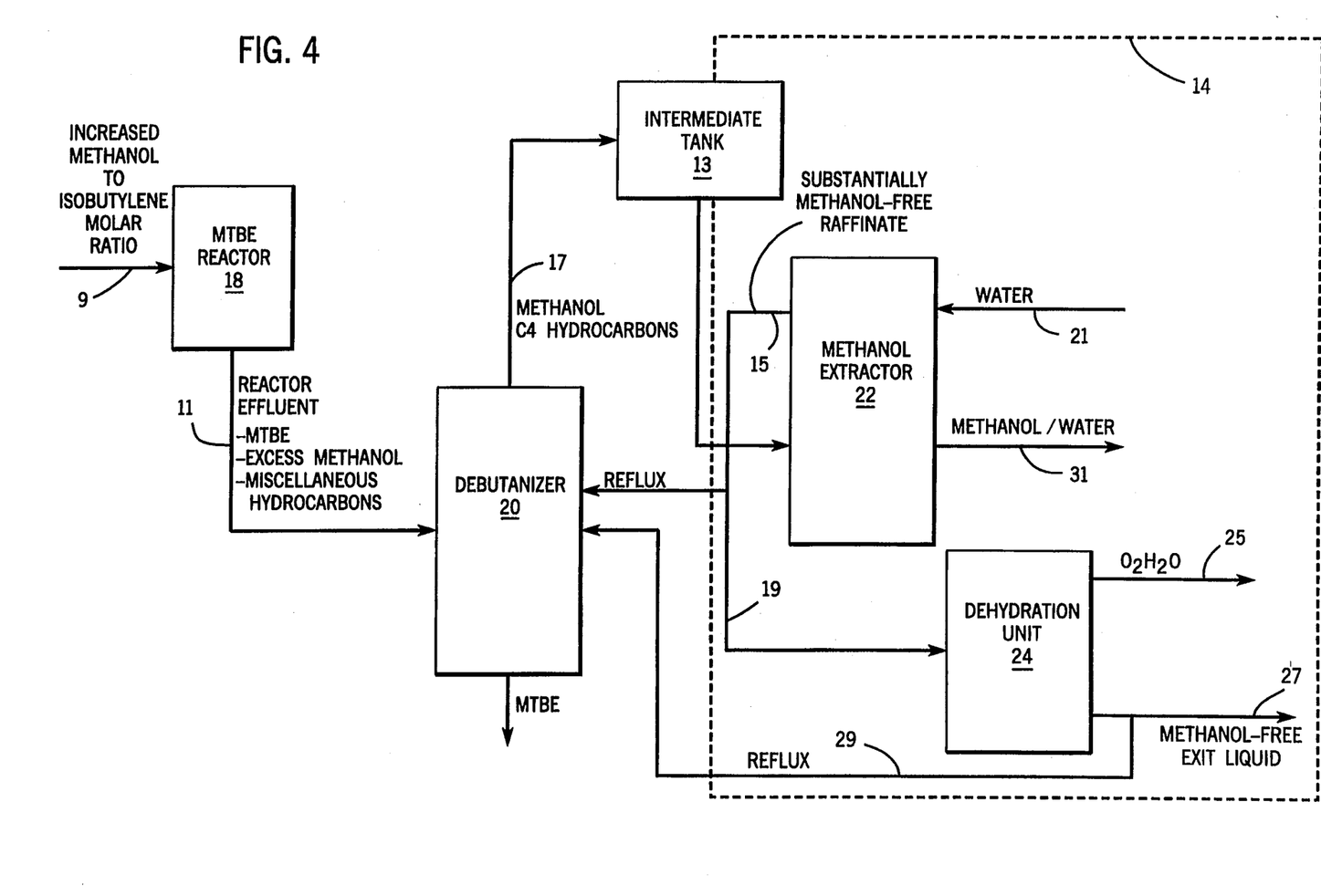
FIG. 4 is a flow chart of the process of the third preferred embodiment of the invention utilizing both the substantially methanol-free raffinate from the methanol removal step and the methanol-free exit liquid from the dehydration step as reflux to the distillation step.
Figure 5:
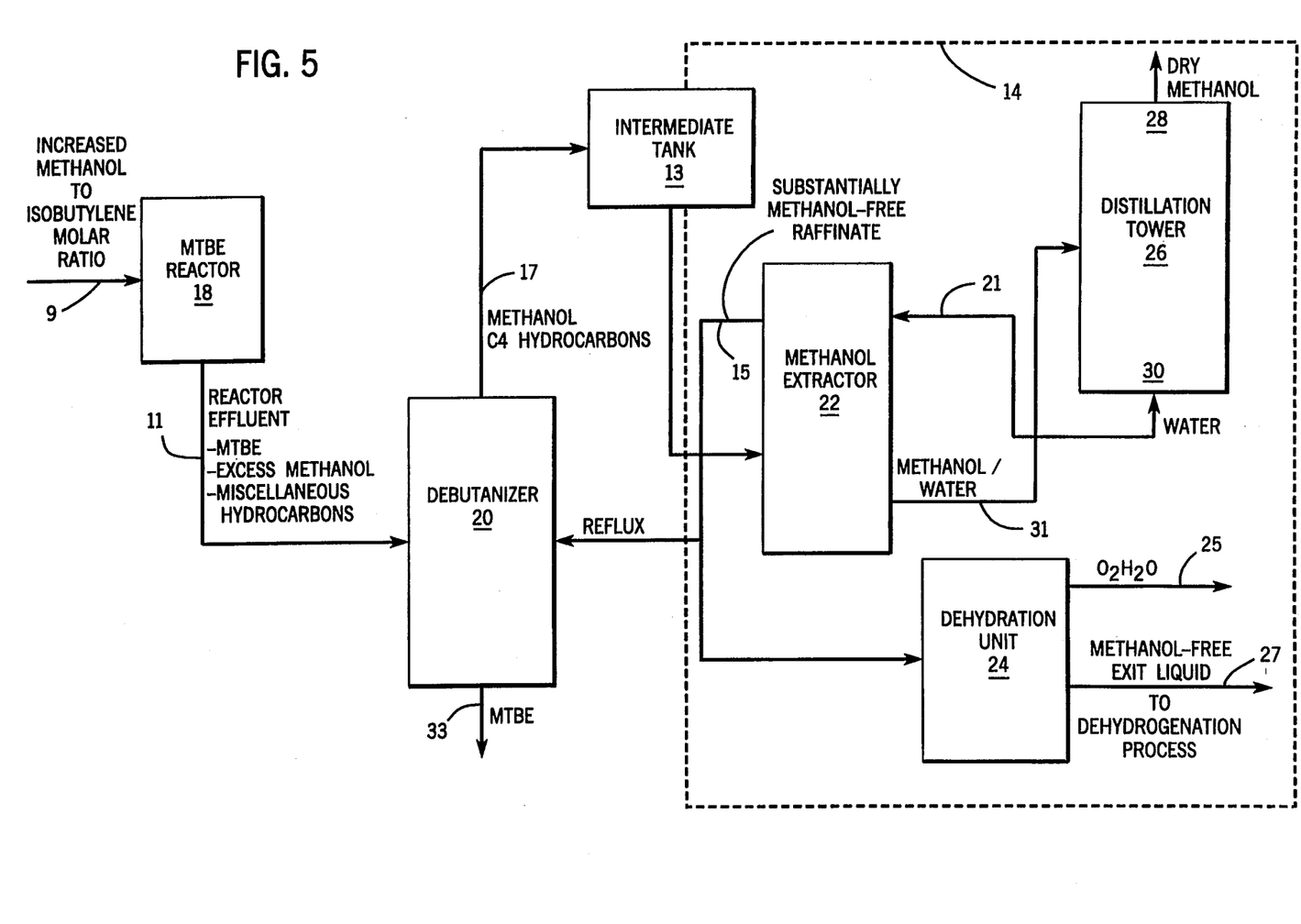
FIG. 5 is a flow chart of the first preferred embodiment with the addition of a second distillation step for separating and recycling the methanol and water recovered from the methanol removal step.
Figure 6:
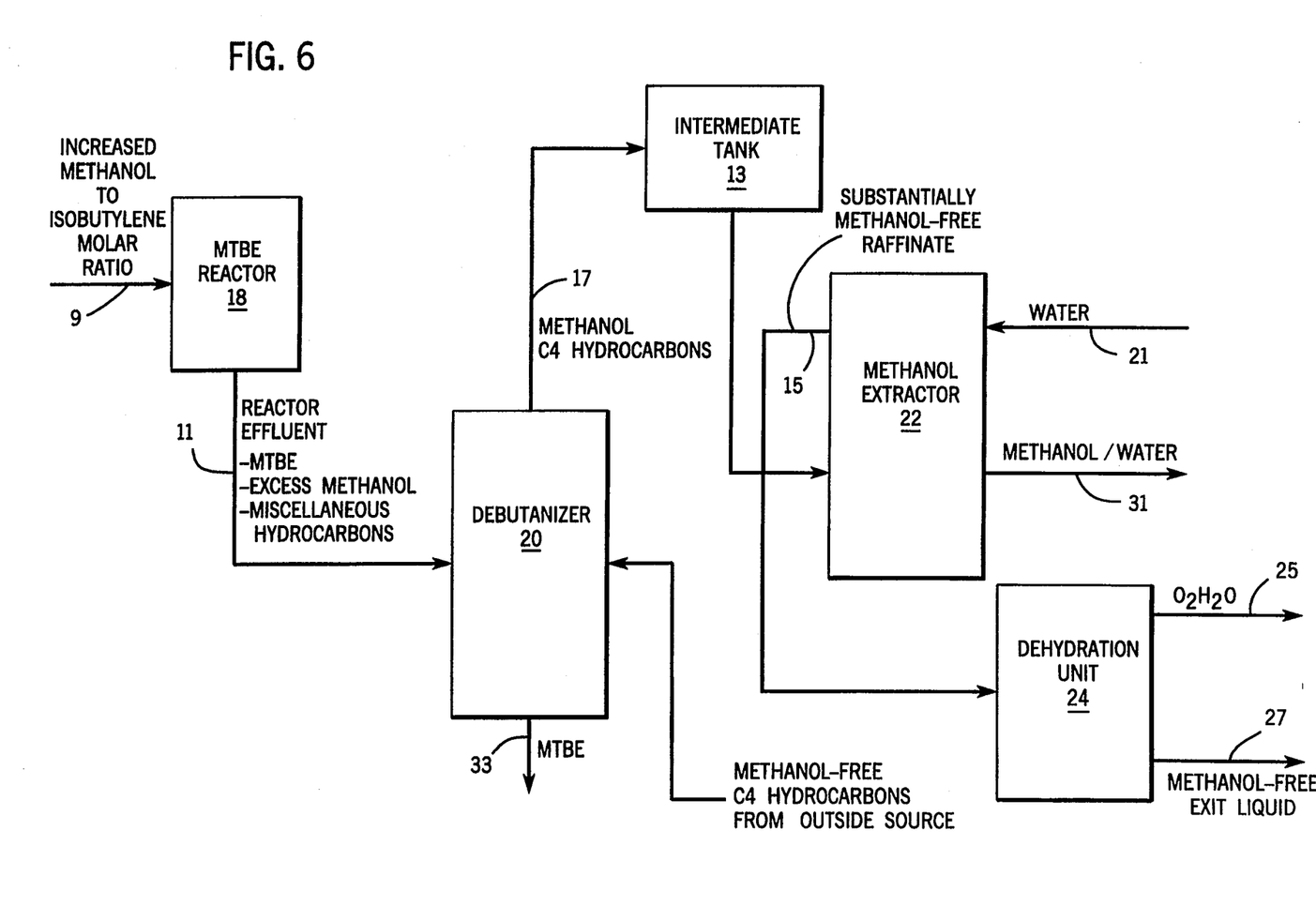
FIG. 6 is a flow chart of the process utilizing methanol-free C4 hydrocarbons from an outside source as reflux to the distillation step.
Figure 7:
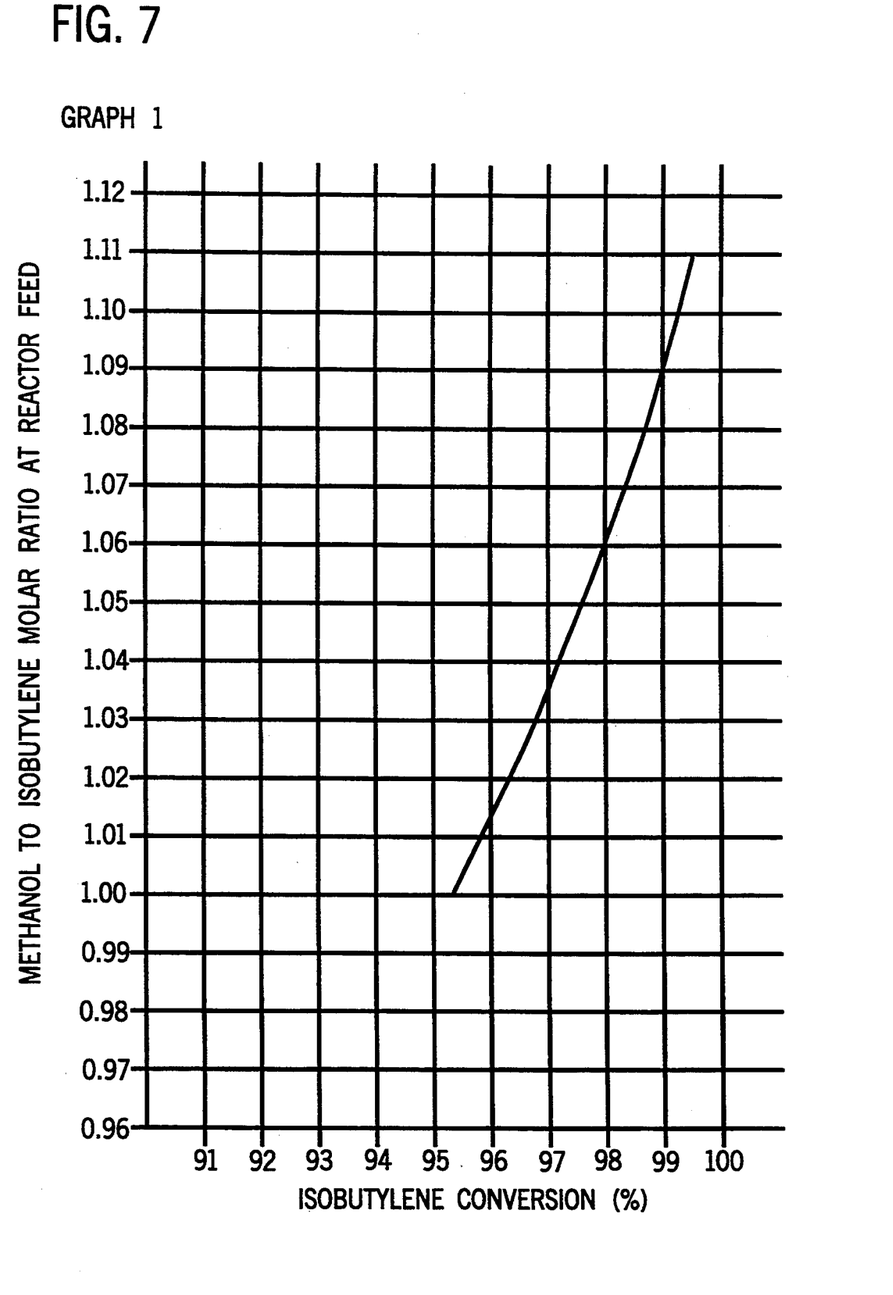
FIG. 7 is a graph showing the methanol to isobutylene molar ratio at the reactor and the corresponding isobutylene conversion percentage.

FIGS. 2, 3 and 4 illustrate a first, second and third preferred embodiment of the invention. FIG. 5 shows the first embodiment with the addition of a distillation process for the methanol/water extract to produce recyclable dry methanol and methanol-free water. The distillation process shown in FIG. 5 may be included in the methanol removal step in any of the three preferred embodiments. An essential feature in all of the embodiments is the inclusion of a feedback loop 16 to feed methanol-free C4 hydrocarbons as reflux to the distillation step. The reflux ratio generally ranges from 1.05 to 1.5 and a feature of the subject invention is that the increased amounts of excess methanol can be removed by using methanol-free C4 hydrocarbons without requiring an increased reflux ratio. A fourth preferred embodiment of the subject invention is illustrated in FIG. 6. In this embodiment, the methanol-free C4 hydrocarbon stream used as reflux to the distillation step is obtained from an outside source.

The initial step in each of embodiments is the reaction of methanol with isobutylene over a fixed bed catalyst to produce an effluent stream containing MTBE, excess methanol and miscellaneous C4 hydrocarbons. The isobutylene is obtained through the dehydrogenation of isobutane. In the reaction step 10, methanol and isobutylene are fed to a MTBE reactor 18 in a methanol to isobutylene molar ratio greater than 1.06 but not exceeding 1.2. By increasing the methanol to isobutylene molar ratio at 9, an isobutylene conversion of more than 98% is obtained. In each of the embodiments, the reactor effluent produced is then fed to a distillation step 12 consisting of a debutanizer 20. In the debutanizer 20, an azeotropic mixture of methanol and C4 hydrocarbons is formed at an azeotropic concentration of 0.065 at 95 psig and recovered at 17 from the top zone of the debutanizer. The overhead vapor is condensed and temporarily stored in an intermediate tank 13.

In each of the preferred embodiments of the invention, the liquid from the intermediate tank 13 is fed to the conversion enhancement system 14. As shown in FIGS. 2, 3 and 4, the system includes a methanol removal apparatus, such as a methanol extractor 22, wherein the methanol may be washed with water to remove the methanol. A substantially methanol-free raffinate and methanol/water extract are recovered at 15 from the extractor 22.

In the first preferred embodiment, at least one portion of the substantially methanol-free raffinate from the extractor 22 is used as reflux to the debutanizer 20 (see FIG. 2). The use of substantially methanol-free raffinate provides C4 hydrocarbons necessary to remove excess methanol while maintaining the azeotropic concentration of 0.065. By maintaining an azeotropic concentration of 0.065, a MTBE product with less than 0.5% methanol content is produced at 33. In the this embodiment, the methanol/water extract recovered from the extractor 22 is discharged at 31 but can be separated and recycled as shown in FIG. 5. The second portion of the raffinate from the extractor 22 is fed to a dehydration unit 24. In the dehydration unit, a small amount of water and oxygenates are removed from the raffinate at 25 and the exit liquid is recycled as indicated at 27 to the dehydrogenation unit 24.

In the second preferred embodiment of the invention shown in FIG. 3, the substantially methanol-free raffinate from the extractor 22 is fed to a dehydration unit 24 where a small amount of water and oxygenates are removed from the raffinate. By removing the water which may contain traces of methanol, the dehydration step eliminates any traces of methanol which may be found in the raffinate. As seen in FIG. 3, at least one portion of the methanol-free exit liquid at 29 from the dehydration unit 24 is used as reflux to the debutanizer 20 while the remaining portion is recycled at 27 to the dehydrogenation process.

FIG. 4 illustrates a third preferred embodiment of the subject invention. The third preferred embodiment utilizes reflux from both the extractor 22 and the dehydration unit 24. In this embodiment, at least one portion of the raffinate recovered from the extractor 22 at 15 is used as reflux to the debutanizer 20. The remaining raffinate continues to the dehydration unit 24 as indicated at 19 and at least one portion of the methanol-free exit liquid from the dehydration unit 24 at 29 is also used as reflux to the debutanizer 20. The remaining exit liquid is recycled at 27 to the dehydrogenation process.

In each of the preferred embodiments, a distillation step to separate methanol and water is preferably included following the methanol removal step. In fact, a stripping tower 26 to separate the methanol/water mixture discharged from the extractor 22 at 31 is typically included in the MTBE process. In order to obtain substantially methanol-free C4's, methanol-free water should be fed to the extractor 22 as at 21. As shown in FIG. 5, the methanol/water extract from the methanol extractor 22 is fed to a distillation tower 26 where it is separated. Methanol-free water is recovered from the bottom 30 of the distillation tower 26 and recycled to the methanol extraction process. In addition, dry methanol is recovered from the top 28 of the tower and can be recycled to the reaction step 10.

While certain features and embodiments have been described in detail herein, it will be readily understood that the invention includes all modifications and enhancements within the scope and spirit of the following claims.

What is claimed is:

1. A process for increasing the conversion of isobutylene to MTBE in the production of MTBE from a reaction of isobutylene with methanol while simultaneously producing a substantially methanol-free MTBE comprising the steps of:
   (a) feeding the methanol and isobutylene to a MTBE reactor at a methanol to isobutylene molar ratio greater than 1.06 but not exceeding 1.2 to achieve a higher isobutylene conversion to MTBE;
   (b) feeding a reactor effluent from the MTBE reactor containing MTBE, methanol and C4 hydrocarbons into a distillation column having a top and a bottom zone, wherein the methanol in the distillation column forms an azeotrope with the C4 hydrocarbons at an azeotropic ratio of 0.065 at 95 psig;
   (c) recovering an overhead product comprising a mixture of methanol and C4 hydrocarbons from the top zone;
   (d) condensing and sending the overhead product to an intermediate tank;
   (e) thereafter removing the methanol from the condensed overhead product;
   (f) recovering a substantially methanol-free raffinate;
   (g) sending the recovered raffinate to a dehydration tower and producing a methanol-free exit liquid;
   (h) using a portion of the exit liquid as reflux to the distillation column; and
   (i) recovering a substantially methanol-free MTBE from the bottom zone of the distillation column.

2. The process in claim 1, wherein using the methanol-free exit liquid as reflux to the distillation column maintains the azeotropic ratio at 0.065.

3. The process in claim 1, wherein the conversion of isobutylene to MTBE in the reaction to produce MTBE is more than 98% and the MTBE produced has less than a 0.5% methanol content.

4. The process in claim 1, wherein the removing step comprises sending the condensed overhead product to an extractor wherein the condensed overhead product is washed with water to remove the methanol.

5. The process in claim 4, wherein a methanol-water mixture is recovered from the extractor.

6. The process in claim 5, further comprising the steps of:
   (a) sending the methanol-water mixture from the extractor to a distillation tower having a top and a bottom section;
   (b) recovering dry methanol from the top section and methanol-free water from the bottom section of the distillation tower; and
   (c) recycling the dry methanol to the reactor and the methanol-free water to the extractor.

7. A process for increasing the conversion of isobutylene to MTBE in the production of MTBE from a reaction of isobutylene with methanol while simultaneously producing a substantially methanol-free MTBE comprising the steps of:
   (a) feeding the methanol and isobutylene to a MTBE reactor at a methanol to isobutylene molar ratio greater than 1.06 but not exceeding 1.2 to achieve a higher isobutylene conversion to MTBE;
   (b) feeding a reactor effluent from the MTBE reactor containing MTBE, methanol and C4 hydrocarbons into a distillation column having a top and a bottom zone, wherein the methanol in the distillation column forms an azeotrope with the C4 hydrocarbons at an azeotropic ratio of 0.065 at 95 psig;
   (c) recovering an overhead product comprising a mixture of methanol and C4 hydrocarbons from the top zone;
   (d) condensing and sending the overhead product to an intermediate tank;
   (e) thereafter removing the methanol from the condensed overhead product;
   (f) recovering a substantially methanol-free raffinate;
   (g) dividing the methanol-free raffinate into a first and second portion;
   (h) using the first portion of the raffinate as reflux to the distillation tower;
   (i) sending the second portion of the recovered raffinate to a dehydration tower; and
   (j) recovering a substantially methanol-free MTBE from the bottom zone of the distillation column.

8. The process of claim 7, steps further comprising:
   (a) obtaining a methanol-free exit liquid from the dehydration tower; and
   (b) using a portion of the methanol-free exit liquid as reflux to the distillation column.

9. The process in claim 7, wherein using the methanol-free exit liquid as reflux to the distillation column maintains the azeotropic ratio at 0.065.

10. The process in claim 7, wherein the conversion of isobutylene to MTBE in the reaction to produce MTBE is more than 98% and the MTBE produced has less than a 0.5% methanol content.

11. The process in claim 7, wherein the removing step comprises sending the condensed overhead product to an extractor wherein the condensed overhead product is washed with water to remove the methanol.

12. The process in claim 11, wherein a methanol-water mixture is recovered from the extractor.

13. The process in claim 12, further comprising the steps of:
   (a) sending the methanol-water mixture from the extractor to a distillation tower having a top and a bottom section;
   (b) recovering dry methanol from the top section and methanol-free water from the bottom section of the distillation tower; and
   (c) recycling the dry methanol to the reactor and the methanol-free water to the extractor.

* * * * *